United States Patent [19]

Schwindeman et al.

[11] Patent Number: 5,663,398

[45] Date of Patent: Sep. 2, 1997

[54] PROCESSES FOR PREPARING FUNCTIONALIZED ALKYLLITHIUM COMPOUNDS

[75] Inventors: James Anthony Schwindeman, Lincolnton; Eric John Granger, Charlotte; Douglas Earl Sutton, Kings Mountain, all of N.C.

[73] Assignee: FMC Corporation, Philadelphia, Pa.

[21] Appl. No.: 711,878

[22] Filed: Sep. 12, 1996

Related U.S. Application Data

[60] Provisional application No. 60/018,343 May 17, 1996.

[51] Int. Cl.$^6$ .................................. C07F 7/08; C07F 7/18
[52] U.S. Cl. ........................... 556/466; 556/470; 556/482; 556/486; 260/665 R; 252/182.12; 252/182.13; 252/182.14; 252/182.3
[58] Field of Search ......................... 556/466, 482, 556/486, 470; 260/665 R; 252/182.12, 182.13, 182.14, 182.3

[56] References Cited

U.S. PATENT DOCUMENTS

| | | |
|---|---|---|
| 5,321,148 | 6/1994 | Schwindeman . |
| 5,331,058 | 7/1994 | Shepherd et al. . |
| 5,340,507 | 8/1994 | Morrison et al. . |
| 5,362,699 | 11/1994 | Shepherd et al. . |
| 5,403,946 | 4/1995 | Schwindeman . |
| 5,416,168 | 5/1995 | Willis et al. . |
| 5,523,447 | 6/1996 | Kamienski et al. ............ 556/466 |
| 5,543,540 | 8/1996 | Schwindseman ............... 556/466 |
| 5,565,526 | 10/1996 | Schwindeman et al. ....... 556/482 X |

*Primary Examiner*—Paul F. Shaver
*Attorney, Agent, or Firm*—Bell, Seltzer, Park & Gibson, P.A.

[57] ABSTRACT

A process for preparing functionalized alkyllithium compounds includes reacting in an inert solvent a protected functionalized alkyl halide with an alkali metal in the presence of a catalytic compound of the formula $$(RR^1R^2M^a)_yA(R^3)_x$$

wherein R, $R^1$ and $R^2$ are each independently selected from the group consisting of hydrogen, halogen, alkyl or alkenyl groups containing one to thirteen carbon atoms; $R^3$ is independently selected from aryl groups containing 6 to 18 carbon atoms, four to six-membered heterocyclic carbon containing groups containing one to two heteroatoms selected from oxygen, nitrogen and sulfur; hydroxyalkyl, alkoxyalkyl, monoalkylaminoalkyl, dialkylaminoalkyl and dialkylphosphinoalkyl groups containing two to thirteen carbon atoms; $M^a$ is an element selected from Group IVA of the Periodic Table of Elements; A is selected from oxygen, sulfur, nitrogen, and phosphorus; x+y equal the valence of A; and x and y may independently have a value from zero to three.

67 Claims, No Drawings

PROCESSES FOR PREPARING FUNCTIONALIZED ALKYLLITHIUM COMPOUNDS

CROSS-REFERENCE TO RELATED APPLICATIONS

This application is related to commonly owned Provisional Application Ser. No. 60/018,343, filed May 17, 1996, now abandoned and claims the benefit of its earlier filing date under 35 U.S.C. 119(e).

FIELD OF THE INVENTION

This invention relates to improved processes for preparing functionalized alkyllithium compounds, and more particularly to catalyzed processes for producing the same.

BACKGROUND OF THE INVENTION

Functionalized organolithium compounds have been used as initiators in the anionic polymerization of olefinic monomers. For example, U.S Pat. No. 5,362,699 discloses novel silyl alkyllithium compounds of the structure:

$$(R^1R^2R^3)Si\text{—}O\text{—}A\text{—}Li$$

wherein A is a branched or straight chain hydrocarbon bridging group containing 3–25 carbon atoms, optionally containing aryl or substituted aryl groups; and $R^1$, $R^2$, and $R^3$ are independently defined as saturated and unsaturated aliphatic and aromatic radicals, and their use as initiators in the anionic polymerization of olefin containing monomers in an inert, hydrocarbon solvent. The preparation of these initiators at higher temperatures is described in U.S. Pat. No. 5,321,148.

Protected silyl initiators are also described in U.S. Pat. No. 5,416,168. This patent describes compounds of the following general structure:

$$(R^1R^2R^3)Si\text{—}O\text{—}CH_2\text{—}A'\text{—}CH_2\text{—}Li$$

wherein each R is methyl, A' is cyclohexyl or CR'R", wherein R' is a linear alkyl group having 1–10 carbon atoms, and R" is hydrogen or a linear alkyl group having 1–10 carbon atoms, and their use as anionic polymerization initiators.

U.S. Pat. No. 5,403,946 describes preparing trimethylsiloxyl functionalized alkyllithium initiators of the structure $(CH_3)_3Si\text{—}O\text{—}R\text{—}Li$, wherein R is selected from alkyl groups containing 2 to 10 carbon atoms and aryl groups containing 6 to 10 carbon atoms by initially reacting a haloalcohol with hexamethyldisilazane and subsequently reacting with lithium.

SUMMARY OF THE INVENTION

The present invention provides a catalyzed process for the preparation of functionalized alkyllithium compounds. Generally, functionalized alkyllithium compounds are prepared by reacting a protected functionalized alkyl halide with an alkali metal in the presence of a catalytic amount of a compound of the formula $$(RR^1R^2M^a)_yA(R^3)_x$$

wherein R, $R^1$ and $R^2$ are each independently selected from the group consisting of hydrogen, halogen, alkyl or alkenyl groups containing one to thirteen carbon atoms; $R^3$ is independently selected from aryl groups containing 6 to 18 carbon atoms, four to six-membered heterocyclic carbon containing groups containing one to two heteroatoms selected from oxygen, nitrogen and sulfur; hydroxyalkyl, alkoxyalkyl, monoalkylaminoalkyl, dialkylaminoalkyl, and dialkylphosphinoalkyl groups containing two to thirteen carbon atoms; $M^a$ is an element selected from Group IVA of the Periodic Table of Elements; A is selected from oxygen, sulfur, nitrogen, and phosphorus; x+y equal the valence of A; and x and y may independently have a value from zero to three.

The addition of the catalysts to alkali metal-halogen exchange reactions can provide higher yields of the functionalized alkyllithium, and less byproduct formation. In addition, the use of catalysts can provide improved quality functionalized alkyllithium compositions, as exemplified by lower soluble chloride, lower turbidity and lower color.

DETAILED DESCRIPTION OF THE INVENTION

Functionalized alkyllithium compounds generally are prepared by reacting a protected functionalized alkyl halide with an alkali metal. The preparation of functionalized alkyllithium compounds is greatly facilitated in accordance with the present invention by addition to the alkali metal-halogen exchange reaction of a catalyst having the following structure:

$$(RR^1R^2M^a)_yA(R^3)_x$$

wherein R, $R^1$ and $R^2$ are each independently selected from the group consisting of hydrogen, halogen, alkyl or alkenyl groups containing one to thirteen carbon atoms; $R^3$ is independently selected from aryl groups containing 6 to 18 carbon atoms, four to six-membered heterocyclic carbon containing groups containing one to two heteroatoms selected from oxygen, nitrogen and sulfur; hydroxyalkyl, alkoxyalkyl, monoalkylaminoalkyl, dialkylaminoalkyl, and dialkylphosphinoalkyl groups containing two to thirteen carbon atoms; $M^a$ is an element selected from Group IVA of the Periodic Table of Elements; A is selected from oxygen, sulfur, nitrogen, and phosphorus; x+y equal the valence of A; and x and y may independently have a value from zero to three.

Catalysts which can be used in accordance with the present invention include, but are not limited to, hydrocarbyl ethers, hydrocarbyl silyl ethers, silyl ethers, hydrocarbylamines, hydrocarbyl silyl amines, organosilylamines, hydrocarbyl sulfides, hydrocarbyl thioethers, hydrocarbyl silyl thioethers, silyl thioethers, hydrocarbyl phosphines, and mixtures thereof.

Hydrocarbyl ethers include cyclic and acyclic ethers, symmetrical and unsymmetrical dialkyl, diaryl and alkylaryl ethers. Such compounds include, for example, cyclic ethers, wherein A is oxygen and $R^3$ is a tetramethylene or a pentamethytene radical, including, but not limited to, tetrahydrofuran, 2-methyl tetrahydrofuran, 1,4-dioxane, tetrahydropyran, and the like, and mixtures thereof; acyclic ethers, wherein $M^a$ is carbon, A is oxygen, and x+y is two, including, but not limited to, diethyl ether, dimethyl ether, methyl-t-butyl ether, di-n-butyl ether, diamyl ether, di-n-hexyl ether, di-n-octyl ether, anisole, butylphenyl ether, diphenyl ether, and the like; and glycol ethers, such as di-methyl, ethyl, and butyl ethers of ethylene glycol, diethylene glycol, triethylene glycol, and the like, and mixtures thereof. Also useful are acetals (1,1-ethers) such as dimethoxymethane and diethoxymethane, and mixtures thereof.

Hydrocarbylsilyl ether and silyl ethers include, but are not limited to, t-butyldimethylisopropoxysilane, trimethylisopropoxysilane, chlorodimethylisopropoxysilane, hexamethyldisiloxane, hexaethyldisiloxane, and the like, and mixtures thereof.

Hydrocarbylamines include, but are not limited to, cyclic and acyclic tertiary amines, wherein $M^a$ is carbon, A is nitrogen, and x+y is three, such as, but not limited to, triethylamine, tributylamine, trihexylamine, trimethylamine, methyldibutylamine, N,N,N'N'-tetramethylethylenediamine, pentamethyldiethylenetriamine, N,N-dimethylaniline, diisopropylethylamine, 1,4-diazabicyclo[2.2.2] octane, N-methylpiperidine, N-ethylpyrrolidine, and the like, and mixtures thereof.

Hydrocarbyl silyl amines include, but are not limited to, cyclic and acyclic tertiary amines, wherein $M^a$ is silicon, A is nitrogen, and x+y is three, such as, but not limited to, heptamethyldisilazane, N,N-diethyltrimethylsilylamine, N,N-dimethyltriethylsilylamine, N-methyl-2,2,5,5-tetramethyl-2,5,-disila-1-azacylclopentane, and the like, and mixtures thereof.

Hydrocarbyl phosphines include, but are not limited to, cyclic and acylic tertiary phosphines, wherein $M^a$ is carbon, A is phosphorus, and x+y is three, such as, but not limited to, triethylphosphine, tributylphosphine, tricyclohexylphosphine, p-methylcyclopentamethylenephosphine, and 1,2-bis (dimethylphosphino) ethane, and the like, and mixtures thereof.

Hydrocarbyl sulfides include, but are not limited to, cyclic and acyclic sulfides, wherein $M^a$ is carbon, A is sulfur, and x+y is 2, including, but not limited to, diethyl sulfide, dibutyl sulfide, tetrahydrothiophene, 1,4-dithiane, 1,4-thioxane, and the like, and mixtures thereof.

The catalytic compound can be used in the alkali metal-halogen exchange reaction in amounts between about 0.1 to about 10 mole percent, based on the alkyl halide. Amounts of as little as one mole percent catalyst to the halide feed mixture can afford the functionalized alkyllithium in higher yield, with less byproduct formation. In addition, the product functionalized alkyllithium reagent solution has higher quality, as exemplified by lower soluble chloride, lower turbidity and lower color.

The catalyst may be added to the lithium metal dispersion prior to or during the halide feed, or mixed with the halide feed and added continuously to the reaction.

For example, one mole percent of hexamethyldisiloxane was added to the halogen feed of 3-(trimethylsilyloxy)-2,2-dimethyl-1-chloropropane in a lithium-halogen exchange reaction. This increased the yield of 3-(trimethylsilyloxy)-2,2-dimethyl-1-propyllithium an average of seven percent over the control. In addition, the amount of 1-methyl-1-trimethylsilyloxymethyl-cyclopropane byproduct was typically lower in the catalyzed reaction, versus the non-catalyzed reaction. Soluble chloride and turbidity were lower in the catalyzed reaction as well, versus the baseline experiment with no catalyst added. These factors can result in improved solution clarity and quality, and thus less interference in reaction applications of the resultant compositions, such as polymerization and organic synthesis.

The alkali metal-halogen reaction can be conducted at temperatures between about 35° C. and about 130° C., and preferably at the solvent reflux temperature. The alkali metal can be lithium, potassium, and sodium metal, and preferably is lithium. The metal may be used in dispersions with particle size ranging from about 10 to 300 microns, although coarser particle sizes can be used. The lithium metal typically contains 0.2 to 0.8 weight percent sodium. The lithium metal can be used in amounts of 90% of theoretical to a 40% excess above the theroretical amount necessary to produce functionalized alkyllithium compounds.

The reaction solvent preferably is an inert solvent, such as a hydrocarbon. Solvents useful in practicing this invention include, but are not limited to, inert liquid alkanes, cycloalkanes and aromatic solvents such as alkanes and cycloalkanes containing five to ten carbon atoms, such as pentane, hexane, cyclohexane, methylcyclohexane, heptane, methylcycloheptane, octane, decane and the like, and aromatic solvents containing six to ten carbon atoms such as toluene, ethylbenzene, p-xylene, m-xylene, o-xylene, n-propylbenzene, isopropylbenzene, n-butylbenzene, t-butylbenzene, and the like, as well as mixtures thereof.

Exemplary protected functionalized alkyl halides include tertiary amino-1-haloalkanes, omega-hydroxy-protected-1-haloalkanes, omega-hydroxy-silyl-protected-1-haloalkanes, and omega-thio-protected-1-haloalkanes, depending upon whether T is N, O or S, respectively (the alkyl portions of the haloalkyl groups contain 3 to 25 carbon atoms). These compounds can be represented generally by the formula

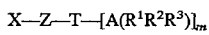

wherein X is halide; Z is a branched or straight chain hydrocarbon group containing 3–25 carbon atoms, optionally containing aryl or substituted aryl groups; T is oxygen, sulfur, or nitrogen; and dialkylphosphinoalkyl is an element selected from Group IVa of the Periodic Table of Elements; $R^1$, $R^2$, and $R^3$ are each independently selected from hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, and cycloalkyl and substituted cycloalkyl containing 5 to 12 carbon atoms; and m is dependent on the valence of T and varies from one when T is oxygen or sulfur to two when T is nitrogen.

Tertiary amino-1-haloalkanes include compounds of the following general structures:

and

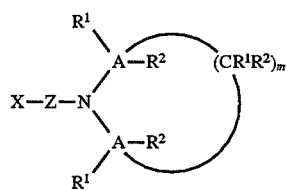

wherein X is halogen, preferably chlorine or bromine; Z is a branched or straight chain hydrocarbon tether or connecting group which contains 3–25 carbon atoms, which tether may also contain aryl or substituted aryl groups; and dialkylphosphinoalkyl is an element selected from Group IVa of the Periodic Table of the Elements; $R^1$, $R^2$, and $R^3$ are independently defined as hydrogen, alkyl, substituted alkyl groups containing lower alkyl, lower alkylthio, and lower dialkylamino groups, aryt or substituted aryl groups containing lower alkyl, lower alkylthio, and lower dialkylamino groups, or cycloalkyl and substituted cycloalkyl groups containing 5 to 12 carbon atoms; and m is an integer from 1 to 7, and their employment as initiators in the anionic polymerization of olefin containing monomers in an inert, hydrocarbon solvent optionally containing a Lewis base. The process reacts selected tertiary amino-1-haloalkanes whose alkyl groups contain 3 to 25 carbon atoms, with alkali metal, preferably lithium, in the presence of the catalyst as described above at a temperature between about 35° C. and about 130° C., preferably at the reflux temperature of an alkane, cycloalkane or aromatic reaction solvent containing 5 to 10 carbon atoms and mixtures of such solvents.

Anionic polymerizations employing the tertiary amine initiators can be conducted in an inert solvent, preferably a non-polar solvent, optionally containing an ethereal modifier, using an olefinic monomer which is an alkenyl-substituted aromatic hydrocarbon or a 1,3-diene at a temperature of about −30° C. to about 150° C. The polymerization reaction proceeds from initiation to propagation and is finally terminated with appropriate reagents so that the polymer is mono-functionally or di-functionally terminated. The polymers may have a molecular weight range of about 1000 to 10,000 but the molecular weight can be higher. Typically 5 to 50 milli-moles of initiator is used per mole of monomer.

Tertiary amino-1-haloalkanes include, but are not limited to, 3-(N,N-dimethylamino)-1-propyl halide, 3-(N,N-dimethylamino)-2-methyl-1-propyl halide, 3-(N,N-dimethylamino)-2,2-dimethyl-1-propyl halide, 4-(N,N-dimethylamino)-1-butyl halide, 5-(N,N-dimethylamino)-1-pentyl halide, 6-(N,N-dimethylamino)-1-hexyl halide, 3-(N,N-diethylamino)-1-propyl halide, 3-(N,N-diethylamino)-2-methyl-1-propyl halide, 3-(N,N-diethylamino)-2,2-dimethyl-1-propyl halide, 4-(N,N-diethylamino)-1-butyl halide, 5-(N,N-diethylamino)-1-pentyl halide, 6-(N,N-diethylamino)-1-hexyl halide, 3-(N-ethyl-N-methylamino)-1-propyl halide, 3-(N-ethyl-N-methylamino)-2-methyl-1-propyl halide, 3-(N-ethyl-N-methylamino)-2,2-dimethyl-1-propyl halide, 4-(N-ethyl-N-methylamino)-1-butyl halide, 5-(N-ethyl-N-methylamino)-1-pentyl halide, 6-(N-ethyl-N-methylamino)-1-hexyl halide, 3-(piperidino)-1-propyl halide, 3-(piperidino)-2-methyl-1-propyl halide, 3-(piperidino)-2,2-dimethyl-1-propyl halide, 4-(piperidino)-1-butyl halide, 5-(piperidino)-1-pentyl halide, 6-(piperidino)-1-hexyl halide, 3-(pyrrolidino)-1-propyl halide, 3-(pyrrolidino)-2-methyl-1-propyl halide, 3-(pyrrolidino)-2,2-dimethyl-1-propyl halide, 4-(pyrrolidino)-1-butyl halide, 5-(pyrrolidino)-1-pentyl halide, 6-(pyrrolidino)-1-hexyl halide, 3-(hexamethyleneimino)-1-propyl halide, 3-(hexamethyleneimino)-2-methyl-1-propyl halide, 3-(hexamethyleneimino)-2,2-dimethyl-1-propyl halide, 4-(hexamethyleneimino)-1-butyl halide, 5-(hexamethyleneimino)-1-pentyl halide, 6-(hexamethyleneimino)-1-hexyl halide, 3-(N-isopropyl-N-methyl)-1-propyl halide, 2-(N-isopropyl-N-methyl)-2-methyl-1-propyl halide, 3-(N-isopropyl-N-methyl)-2,2-dimethyl-1-propyl halide, and 4-(N-isopropyl-N-methyl)-1-butyl halide. The halo- or halide group is preferably selected from chlorine and bromine.

Omega-hydroxy-protected-1-haloalkanes can have the following general structure:

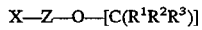

X—Z—O—[C(R$^1$R$^2$R$^3$)]

wherein X is halogen, preferably chlorine or bromine; Z is a branched or straight chain hydrocarbon group which contains 3–25 carbon atoms, optionally containing aryl or substituted aryl groups; and R$^1$, R$^2$, and R$^3$ are independently defined as hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, or cycloalkyl and substituted cycloalkyl groups containing 5 to 12 carbon atoms, and their employment as initiators in the anionic polymerization of olefin containing monomers in an inert, hydrocarbon solvent optionally containing a Lewis base. The process reacts selected omega-hydroxy-protected-1-haloalkanes whose alkyl groups contain 3 to 25 carbon atoms, with alkali metal, preferably lithuim, in the presence of the catalyst as described above at a temperature between about 35° C. and about 130° C., preferably at the reflux temperature of an alkane, cycloalkane or aromatic reaction solvent containing 5 to 10 carbon atoms and mixtures of such solvents.

Anionic polymerizations employing the monofunctional ether initiators can be conducted in an inert solvent, preferably a non-polar solvent, optionally containing an ethereal modifier, using an olefinic monomer which is an alkenyl-substituted aromatic hydrocarbon or a 1,3-diene at a temperature of about −30° C. to about 150° C. The polymerization reaction proceeds from initiation to propagation and is finally terminated with appropriate reagents so that the polymer is mono-functionally or di-functionally terminated. The polymers may have a molecular weight range of about 1000 to 10,000 but the molecular weight can be higher. Typically 5 to 50 milli-moles of initiator is used per mole of monomer.

The precursor omega-protected-1-haloalkanes (halides) can be prepared from the corresponding haloalcohol by standard literature methods. For example, 3-(1,1-dimethylethoxy)-1-chloropropane can be synthesized by the reaction of 3-chloro-1-propanol with 2-methylpropene according to the method of A. Alexakis, M. Gardette, and S. Colin, Tetrahedron Letters, 29, 1988, 2951. The method of B. Figadere, X. Franck and A. Cave, Tetrahedron Letters, 34, 1993, 5893, which involves the reaction of the appropriate alcohol with 2-methyl-2-butene catalyzed by boron trifluoride etherate, can be employed for the preparation of the t-amyl ethers. The alkoxy, alkylthio or dialkylamino substituted ethers, for example 6-[3-(methylthio)-1-propyloxy]-1-chlorohexane, can be synthesized by reaction of the corresponding substituted alcohol, for instance 3-methylthio-1-propanol, with an alpha-bromo-omega-chloroalkane, for instance 1-bromo-6-hexane, according to the method of J. Almena, F. Foubelo and M. Yus, Tetrahedron, 51, 1995, 11883. The compound 4-(methoxy)-1-chlorobutane, and the higher analogs, can be synthesized by the ring opening reaction of tetrahydrofuran with thionyl chloride and methanol, according to the procedure of T. Ferrari and P. Vogel, SYNLETT, 1991, 233. The triphenylmethyl protected compounds, for example 3-(triphenylmethoxy)-1-chloropropane, can be prepared by the reaction of the haloalcohol with triphenylmethylchloride, according to the method of S. K. Chaudhary and O. Hernandez, Tetrahedron Letters, 1979, 95.

Omega-hydroxy-protected-1-haloalkanes include, but are not limited to, 3-(1,1-dimethylethoxy)-1-propyl halide, 3-(1,1-dimethylethoxy)-2-methyl-1-propyl halide, 3-(1,1-dimethylethoxy)-2,2-dimethyl-1-propyl halide, 4-(1,1-dimethylethoxy)-1-butyl halide, 5-(1,1-dimethylethoxy)-1-pentyl halide, 6-(1,t-dimethylethoxy)-1-hexyl halide, 8-(1,1-dimethylethoxy)-1-octyl halide, 3-(1,1-dimethylpropoxy)-1-propyl halide, 3-(1,1-dimethylpropoxy)-2-methyl-1-propyl halide, 3-(1,1-dimethylpropoxy)-2,2-dimethyl-1-propyl halide, 4-(1,1-dimethylpropoxy)-1-butyl halide, 5-(1,1-dimethylpropoxy)-1-pentyl halide, 6-(1,1-dimethylpropoxy)-1-hexyl halide, 8-(1,1-dimethylpropoxy)-1-octyl halide, 4-(methoxy)-1-butyl halide, 4-(ethoxy)-1-butyl halide, 4-(propyloxy)-1-butyl halide, 4-(1-methylethoxy)-1-butyl halide, 3-(triphenylmethoxy)-2,2-dimethyl-1-propyl halide, 4-(triphenylmethoxy)-1-butyl halide, 3-[3-(dimethylamino)-1-propyloxy]-1-propyl halide, 3-[2-(dimethylamino)-1-ethoxy]-1-propyl halide, 3-[2-(diethylamino)-1-ethoxy]-1-propyl halide, 3-[2-(diisopropyl)amino]-1-ethoxy]-1-propyl halide, 3-[2-(1-piperidino)-1-ethoxy]-1-propyl halide, 3-[2-(1-pyrrolidino)-1-ethoxy]-1-propyl halide, 4-[3-(dimethylamino)-1-propyloxy]-1-butyl halide, 6-[2-(1-piperidino)-1-ethoxy]-1-hexyl halide, 3-[2-(methoxy)-1-ethoxy]-1-propyl halide, 3-[2-(ethoxy)-1-ethoxy]-1-propyl halide, 4-[2-(methoxy)-1-ethoxy]-1-butyl halide, 5-[2-(ethoxy)-1-ethoxy]-1-pentyl halide, 3-[3-(methylthio)-1-propyloxy]-1-propyl halide, 3-[4-(methylthio)-1-butyloxy]-1-propyl halide, 3-(methylthiomethoxy)-1-propyl halide, 6-[3-(methylthio)-1-propyloxy]-1-hexyl halide, 3-[4-(methoxy)-benzyloxy]-1-propyl halide, 3-[4-(1,1-dimethylethoxy)-benzyloxy]-1-propyl halide, 3-[2,4-(dimethoxy)-benzyloxy]-1-propyl halide, 8-[4-(methoxy)-benzyloxy]-1-octyl halide, 4-[4-(methylthio)-benzyloxy]-1-butyl halide, 3-[4-(dimethylamino)-benzyloxy]-1-propyl halide, 6-[4-(dimethylamino)-benzyloxy]-1-hexyl halide, 5-(triphenylmethoxy)-1-pentyl halide, 6-(triphenylmethoxy)-1-hexyl halide, and 8-(triphenylmethoxy)-1-octyl halide. The halo- or halide group is preferably selected from chlorine and bromine.

U.S. Pat. No. 5,362,699 discloses a process for the preparation of hydrocarbon solutions of monofunctional ether initiators derived from omega-hydroxy-silyl-protected-1-haloalkanes of the following general structure:

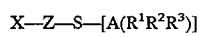

X—Z—O—[Si(R¹R²R³)]

wherein X is halogen, preferably chlorine or bromine; Z is a branched or straight chain hydrocarbon group which contains 3–25 carbon atoms, optionally containing aryl or substituted aryl groups; and R¹, R², and R³ are independently defined as saturated and unsaturated aliphatic and aromatic radicals, and their employment as initiators in the anionic polymerization of olefin containing monomers in an inert, hydrocarbon solvent optionally containing a Lewis base. The process reacts selected omega-hydroxy-silyl-protected-1-haloalkanes whose alkyl groups contain 3 to 25 carbon atoms, with alkali metal, preferably lithium, in the presence of the catalyst as described above at a temperature between about 25° C. and about 40° C., in an alkane or cycloalkane reaction solvent containing 5 to 10 carbon atoms and mixtures of such solvents.

Anionic polymerizations employing the monofunctional siloxy ether initiators can be conducted in an inert solvent, preferably a non-polar solvent, optionally containing an ethereal modifier, using an olefinic monomer which is an alkenylsubstituted aromatic hydrocarbon or a 1,3-diene at a temperature of about −30° C. to about 150° C. The polymerization reaction proceeds from initiation to propagation and is finally terminated with appropriate reagents so that the polymer is mono-functionally or di-functionally terminated. The polymers may have a molecular weight range of about 1000 to 10,000 but the molecular weight can be higher. Typically 5 to 50 milli-moles of initiator is used per mole of monomer.

Omega-hydroxy-silyl-protected-1-haloalkanes include, but are not limited to, 3-(t-butyldimethylsilyloxy)-1-propyl halide, 3-(t-butyldimethyl-silyloxy)-2-methyl-1-propyl halide, 3-(t-butyldimethylsilyloxy)-2,2-dimethyl-1-propyl halide, 4-(t-butyldimethylsilyloxy)-1-butyl halide, 5-(t-butyldimethylsilyloxy)-1-pentyl halide, 6-(t-butyldimethylsilyloxy)-1-hexyl halide, 8-(t-butyldimethylsilyloxy)-1-octyl halide, 3-(t-butyldiphenylsilyloxy)-1-propyl halide, 3-(t-butyldiphenylsilyloxy)-2-methyl-1-propyl halide, 3-(t-butyldiphenylsilyloxy)-2,2-dimethyl-1-propyl halide, 4-(t-butyldiphenylsilyloxy)-1-butyl halide, 6-(t-butyldiphenylsilyloxy)-1-hexyl halide and 3-(trimethylsilyloxy)-2,2-dimethyl-1-propyl halide. The halo- or halide group is preferably selected from chlorine and bromine.

Monofunctional thioether initiators can be derived from omega-thio-protected-1-haloalkanes of the following general structure:

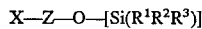

X—Z—S—[A(R¹R²R³)]

wherein X is halogen, preferably chlorine or bromine; Z is a branched or straight chain hydrocarbon group which contains 3–25 carbon atoms, optionally containing aryl or substituted aryl groups; [A(R¹R²R³)] is a protecting group in which A is an element selected from Group IVa of the Periodic Table of the Elements, and R¹, R², and R³ are independently defined as hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, or cycloalkyl and substituted cycloalkyl groups containing 5 to 12 carbon atoms, and their employment as initiators in the anionic polymerization of olefin containing monomers in an inert, hydrocarbon solvent optionally containing a Lewis base. The process reacts selected omega-thio-protected-1-haloalkyls whose alkyl groups contain 3 to 25 carbon atoms, with alkali metal, preferably lithium, in the presence of the catalyst as described above at a temperature between about 35° C. and about 130° C., preferably at the reflux temperature of an alkane, cycloalkane or aromatic reaction solvent containing 5 to 10 carbon atoms and mixtures of such solvents.

Anionic polymerizations employing the monofunctional thioether initiators can be conducted in an inert solvent, preferably a non-polar solvent, optionally containing an ethereal modifier, using an olefinic monomer which is an alkenylsubstituted aromatic hydrocarbon or a 1,3-diene at a temperature of about −30° C. to about 150° C. The polymerization reaction proceeds from initiation to propagation and is finally terminated with appropriate reagents so that the polymer is mono-functionally or di-functionally terminated. The polymers may have a molecular weight range of about 1000 to 10,000 but the molecular weight can be higher. Typically 5 to 50 milli-moles of initiator is used per mole of monomer.

The initiator precursor, omega-thio-protected-1-haloalkanes (halides), can be prepared from the corresponding halothiol by standard literature methods. For example, 3-(1,1-dimethylethylthio)-1-propylchloride can be synthesized by the reaction of 3-chloro-1-propanethiol with 2-methylpropene according to the method of A. Alexakis, M. Gardette, and S. Colin, Tetrahedron Letters, 29, 1988, 2951. Alternatively, reaction of 1,1-dimethylethylthiol with 1-bromo-3-chloropropane and a base affords 3-(1,1-dimethylethylthio)-1-propylchloride. The method of B. Figadere, X. Franck and A. Cave, Tetrahedron Letters, 34, 1993, 5893, which involves the reaction of the appropriate thiol with 2-methyl-2-butene catalyzed by boron trifluoride etherate, can be employed for the preparation of the t-amyl thioethers. Additionally, 5-(cyclohexylthio)-1-pentylhalide and the like, can be prepared by the method of J. Almena, F. Foubelo, and M. Yus, Tetrahedron, 51, 1995, 11883. This synthesis involves the reaction of the appropriate thiol with an alkyllithium, then reaction of the lithium salt with the corresponding alpha, omega dihalide. 3-(Methylthio)-1-propylchloride can be prepared by chlorination of the corresponding alcohol with thionyl chloride, as taught by D. F. Taber and Y. Wang, J. Org, Chem., 58, 1993, 6470. Methoxymethylthio compounds, such as 6-(methoxymethylthio)-1-hexylchloride, can be prepared by the reaction of the omega-chloro-thiol with bromochloromethane, methanol, and potassium hydroxide, by the method of F. D. Toste and I. W. J. Still, Synlett, 1995, 159. T-Butyldimethylsilyl protected compounds, for example 4-(t-butyldimethylsilylthio)-1-butylhalide, can be prepared from t-butyldimethylchlorosilane, and the corresponding thiol, according to the method described in U.S. Pat. No. 5,493,044.

Omega-thio-protected-1-haloalkanes include, but are not limited to, 3-(methylthio)-1-propylhalide, 3-(methylthio)-2-methyl-1-propylhalide, 3-(methylthio)-2,2-dimethyl-1-propylhalide, 4-(methylthio)-1-butylhalide, 5-(methylthio)-1-pentylhalide, 6-(methylthio)-1-hexylhalide, 8-(methylthio)-1-octylhalide, 3-(methoxymethylthio)-1-propylhalide, 3-(methoxymethylthio)-2-methyl-1-propylhalide, 3-(methoxymethylthio)-2,2-dimethyl-1-propylhalide, 4-(methoxymethylthio)-1-butylhalide, 5-(methoxymethylthio)-1-pentylhalide, 6-(methoxymethylthio)-1-hexylhalide, 8-(methoxymethylthio)-1-octylhalide, 3-(1,1-dimethylethylthio)-1-propylhalide, 3-(1,1-dimethylethylthio)-2-methyl-1-propylhalide, 3-(1,1-dimethylethylthio)-2,2-dimethyl-1-propylhalide, 4-(1,1-dimethylethylthio)-1-butylhalide, 5-(1,1-dimethylethylthio)-1-pentylhalide, 6-(1,1-dimethylethylthio)-1-hexylhalide, 8-(1,1-dimethylethylthio)-1-octylhalide, 3-(1,1-dimethylpropylthio)-1-propylhalide, 3-(1,1-dimethylpropylthio)-2-methyl-1-propylhalide, 3-(1,1-dimethylpropylthio)-2,2-dimethyl-1-propylhalide, 4-(1,1-dimethylpropylthio)-1-butylhalide, 5-(1,1-dimethylpropylthio)-1-pentylhalide, 6-(1,1-dimethylpropylthio)-1-hexylhalide, 8-(1,1-dimethylpropylthio)-1-octylhalide, 3-(cyelopentylthio)-1-propylhalide, 3-(cyclopentylthio)-2-methyl-1-propylhalide, 3-(cyclopentylthio)-2,2-dimethyl-1-propylhalide, 4-(cyclopentylthio)-1-butylhalide, 5-(cyclopentylthio)-1-pentylhatide, 6-(cyclopentylthio)-1-hexylhalide, 8-(cyclopentylthio)-1-octylhalide, 3-(cyclohexylthio)-1-propylhalide, 3-(cyclohexylthio)-2-methyl-1-propylhalide, 3-(cyclohexylthio)-2,2-dimethyl-1-propylhalide, 4-(cyclohexylthio)-1-butylhalide, 5-(cyclohexylthio)-1-pentylhalide, 6-(cyclohexylthio)-1-hexylhalide, 8-(cyclohexylthio)-1-octylhalide, 3-(t-butyldimethylsilylthio)-1-propylhalide, 3-(t-butyldimethylsilylthio)-2-methyl-1-propylhalide, 3-(t-butyldimethylsilylthio)-2,2-dimethyl-1-propylhalide, 3-(t-butyldimethylsilylthio)-2-methyl-1-propylhalide, 4-(t-butyldimethylsilylthio)-1-butylhalide, 6-(t-butyldimethylsilylthio)-1-hexylhalide and 3-(trimethylsilylthio)-2,2-dimethyl-1-propylhalide. The halo- or halide group is preferably selected from chlorine and bromine.

Exemplary functionalized alkyllithium initiators prepared in accordance with the present invention can be represented by the following formula:

wherein M is an alkali metal; Q is a saturated or unsaturated hydrocarbyl group derived by incorporation of a compound selected from the group consisting of conjugated diene hydrocarbons, alkenylsubstituted aromatic hydrocarbons, and mixtures thereof; n is an integer from 0 to 5; Z is a branched or straight chain hydrocarbon group which contains 3–25 carbon atoms, optionally containing aryl or substituted aryl groups; T is a hetero atom, e.g., oxygen, sulfur, or nitrogen; A is an element selected from Group IVa of the Periodic Table of Elements; $R^1$, $R^2$, and $R^3$ are independently selected from hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, and cycloalkyl and substituted cycloalkyl containing 5 to 12 carbon atoms; and m is dependent on the valence of J and varies from one when J is oxygen or sulfur to two when J is nitrogen.

Functionalized alkyllithium initiators of Formula (I) include omega-(tert-alkoxy)-1-alkyllithiums, omega-(tert-alkoxy)-1-alkyllithiums chain extended with conjugated alkadienes, alkenylsubstituted aromatic hydrocarbons, and mixtures thereof, omega-(tert-alkylthio)-1-alkyllithiums, omega-(tert-alkylthio)-1-alkyllithiums chain extended with conjugated alkadienes, alkenylsubstituted aromatic hydrocarbons, and mixtures thereof, omega-(tert-butyldimethylsilyloxy)-1-alkyllithiums, omega-(tert-butyldimethylsilylthio)-1-alkyllithiums, omega-(dialkylamino)-1-alkyllithiums, omega-(dialkylamino)-1-alkyllithiums chain-extended with conjugated alkadienes, alkenylsubstituted aromatic hydrocarbons, and mixtures thereof, and omega-(bis-tert-alkylsilylamino)-1-alkyllithiums.

Examples of functionalized alkyllithium initiators (I) include, but are not limited to, tert-alkoxy-alkyllithiums such as 3-(1,1-dimethylethoxy)-1-propyllithium and its more hydrocarbon-soluble isoprene chain-extended oligomeric analog (n=2), 3-(tert-butyldimethylsilyloxy)-1-propyllithium (n=0), tert-alkylthio-alkyllithiums such as 3-(1,1-dimethylethylthio)-1-propyltithium and its more hydrocarbon-soluble isoprene chain-extended oligomeric analog (n=2), 3-(dimethylamino)-1-propyllithium and its more hydrocarbon-soluble isoprene chain-extended oligomeric analog (n=2) and 3-(di-tert-butyldimethylsilylamino)-1-propyllithium, and mixtures thereof. Further examples of protected functionalized initiators include, but are not limited to, 3-(1,1-dimethylethoxy)-1-propyllithium, 3-(1,1-dimethylethoxy)-2-methyl-1-propyllithium, 3-(1,1-dimethylethoxy)-2,2-dimethyl-1-propyllithium, 4-(1,1-dimethylethoxy)-1-butyllithium, 5-(1,1-dimethylethoxy)-1-pentyllithium, 6-(1,1-dimethylethoxy)-1-hexyllithium, 8-(1,1-dimethylethoxy)-1-octyllithium, 3-(1,1-dimethylpropoxy)-1-propyllithium, 3-(1,1-dimethylpropoxy)-2-methyl-1-propyllithium, 3-(1,1-dimethylpropoxy)-2,2-dimethyl-1-propyllithium, 4-(1,1-dimethylpropoxy)-1-butyllithium, 5-(1,1-dimethylpropoxy)-1-pentyllithium, 6-(1,1-dimethylpropoxy)-1-hexyllithium, 8-(1,1-dimethylpropoxy)-1-octyllithium, 3-(t-butyldimethylsilyloxy)-1-propyllithium, 3-(t-butyldimethylsilyloxy)-2-methyl-1-propyllithium, 3-(t-butyldimethylsilyloxy)-2,2-dimethyl-1-propyllithium, 4-(t-butyldimethylbilyloxy)-1-butyllithium, 5-(t-butyldimethylsilyloxy)-1-pentyllithium, 6-(t-butyldimethylsilyloxy)-1-hexyllithium, 8-(t-butyldimethylsilyloxy)-1-octyllithium and 3-(trimethylsilyloxy)-2,2-dimethyl-1-propyllithium, 3-(dimethylamino)-1-propyllithium, 3-(dimethylamino)-2-methyl-1-propyllithium, 3-(dimethylamino)-2,2-dimethyl-1-propyllithium, 4-(dimethylamino)-1-butyllithium, 5-(dimethylamino)-1-pentyllithium, 6-(dimethylamino)-1-hexyllithium, 8-(dimethylamino)-1-propyllithium, 4-(ethoxy)-1-butyllithium, 4-(propyloxy)-1-butyllithium, 4-(1-methylethoxy)-1-butyllithium, 3-(triphenylmethoxy)-

2,2-dimethyl-1-propyllithium, 4-(triphenylmethoxy)-1-butyllithium, 3-[3-(dimethylamino)-1-propyloxy]-1-propyllithium, 3-[2-(dimethylamino)-1-ethoxy]-1-propyllithium, 3-[2-(diethylamino)-1-ethoxy]-1-propyllithium, 3-[2-(diisopropyl)amino]-1-ethoxy]-1-propyllithium, 3-[2-(1-piperidino)-1-ethoxy]-1-propyllithium, 3-[2-(1-pyrrolidino)-1-ethoxy]-1-propyllithium, 4-[3-(dimethylamino)-1-propyloxy]-1-butyllithium, 6-[2-(1-piperidino)-1-ethoxy]-1-hexyllithium, 3-[2-(methoxy)-1-ethoxy]-1-propyllithium, 3-[2-(ethoxy)-1-ethoxy]-1-propyllithium, 4-[2-(methoxy)-1-ethoxy]-1-butyllithium, 5-[2-(ethoxy)-1-ethoxy]-1-pentyllithium, 3-[3-(methylthio)-1-propyloxy]-1-propyllithium, 3-[4-(methylthio)-1-butyloxy]-1-propyllithium, 3-(methylthiomethoxy)-1-propyllithium, 6-[3-(methylthio)-1-propyloxy]-1-hexyllithium, 3-[4-(methoxy)-benzyloxy]-1-propyllithium, 3-[4-(1,1-dimethylethoxy)-benzyloxy]-1-propyllithium, 3-[2,4-(dimethoxy)-benzyloxy]-1-propyllithium, 8-[4-(methoxy)-benzyloxy]-1-octyllithium, 4-[4-(methylthio)-benzyloxy]-1-butyllithium, 3-[4-(dimethylamino)-benzyloxy]-1-propyllithium, 6-[4-(dimethylamino)-benzyloxy]-1-hexyllithium, 5-(triphenylmethoxy)-1-pentyllithium, 6-(triphenylmethoxy)-1-hexyllithium, and 8-(triphenylmethoxy)-1-octyllithium, 3-(hexamethyleneimino)-1-propyllithium, 4-(hexamethyleneimino)-1-butyllithium, 5-(hexamethyleneimino)-1-pentyllithium, 6-(hexamethyleneimino)-1-hexyllithium, 8-(hexamethyleneimino)-1-octyllithium, 3-(t-butyldimethylsilylthio)-1-propyllithium, 3-(t-butyldimethylsilylthio)-2-methyl-1-propyllithium, 3-(t-butyldimethylsilylthio)-2,2-dimethyl-1-propyllithium, 4-(t-butyldimethylsilylthio)-1-butyllithium, 6-(t-butyldimethylsilylthio)-1-hexyllithium, 3-(trimethylsilylthio)-2,2-dimethyl-1-propyllithium, 3-(1,1-dimethylethylthio)-1-propyllithium, 3-(1,1-dimethylethylthio)-2-methyl-1-propyllithium, 3-(1,1-dimethylethylthio)-2,2-dimethyl-1-propyllithium, 3-(tert-butylthio)-1-propyllithum, 4-(1,1-dimethylethylthio)-1-butyllithium, 5-(1,1-dimethylethylthio)-1-pentyllithium, 6-(1,1-dimethylethylthio)-1-hexyllithium, 8-(1,1-dimethylethylthio)-1-octyllithium, 3-(1,1-dimethylpropylthio)-1-propyllithium, 3-(1,1-dimethylpropylthio)-2-methyl-1-propyllithium, 3-(1,1-dimethylpropylthio)-2,2-dimethyl-1-propyllithium, 3-(tert-butylthio)-1-propyllithium, 4-(1,1-dimethylpropylthio)-1-butyllithium, 5-(1,1-dimethylpropylthio)-1-pentyllithium, 6-(1,1-dimethylpropylthio)-1-hexyllithium, and 8-(1,1-dimethylpropylthio)-1-octyllithium and their more hydrocarbon soluble conjugated alkadiene, alkenylsubstituted aromatic hydrocarbon, and mixtures thereof, chain extended oligomeric analogs (n=1–5).

Initiators of Formula (I) having an extended chain (denoted as $Q_n$) can be prepared by reaction of functionalized alkyllithium compounds of Formula (I) above wherein n is zero with conjugated alkadienes (such as butadiene or isoprene), alkenylsubstituted aromatic hydrocarbons (such as styrene or alpha-methylstyrene), and mixtures thereof, to form an extended hydrocarbon chain between M and Z.

The functionalized alkyllithium compounds described herein can be used as initiators in the anionic polymerization of olefinic monomers to prepare functionalized, telechelic, hetero-telechelic, and multi-branched and star polymers. Anionically polymerizable olefinic monomers include alkenylsubstituted aromatic hydrocarbons and 1,3-dienes. The monomers may be polymerized singly, or in admixture with each other or with other dienes or alkenylsubstituted aromatic hydrocarbons to form random or tapered copolymers, or by charging the compounds to the reaction mixture sequentially, either with each other or with other dienes or alkenylsubstituted aromatic hydrocarbons, to form block copolymers. Examples of suitable conjugated diene hydrocarbons include, but are not limited to, 1,3-butadiene, isoprene, 2,3-dimethyl-1,3-butadiene, 1,3-pentadiene, myrcene, 2-methyl-3-ethyl-1,3-butadiene, 2-methyl-3-ethyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, and 2-methyl-3-isopropyl-1,3-butadiene. Examples of polymerizable alkenylsubstituted aromatic hydrocarbons include, but are not limited to, styrene, alpha-methylstyrene, vinyltoluene, 2-vinylpyridine, 4-vinylpyridine, 1-vinylnaphthalene, 2-vinylnaphthalene, 1-alpha-methylvinylnaphthalene, 2-alpha-methylvinylnaphthalene, 1,2-diphenyl-4-methyl-1-hexene and mixtures of these, as well as alkyl, cycloalkyl, aryl, alkylaryl and arylalkyl derivatives thereof in which the total number of carbon atoms in the combined hydrocarbon constituents is generally not greater than 18. Examples of these latter compounds include 3-methylstyrene, 3,5-diethylstyrene, 4-tert-butylstyrene, 2-ethyl-4-benzylstyrene, 4-phenylstyrene, 4-p-tolylstyrene, 2,4-divinyltoluene and 4,5-dimethyl-1-vinylnaphthalene. U.S. Pat. No. 3,377,404, incorporated herein by reference in its entirety, discloses suitable additional alkenylsubstituted aromatic hydrocarbons.

The following examples further illustrate the invention. In the examples, the following analytical techniques were used to evaluate the improved process of the invention.

COLOR

Color was measured visually by comparing a sample to Platinum-Cobalt (PC) liquid color standards (ASTM D 1209) or BYK-Gardner (BG) liquid color standards (ASTM D 1544). Color was reported as the number of the standard which most closely matches the sample in intensity of color. The PC color standards are gradations of a pale yellow hue. The BG color standards range in hue from pale yellow to dark brown. Color is reported as a five-digit number with three data fields, the test method identifier, the test result, and the off-color descriptor, as follows:

First Digit

Test Method Identifier

The first digit is reported as a value of 1 if the PC scale for color was used, and as a value of 2 if the BG scale for color was used.

Second, Third, and Fourth Digits

Test Result

Test result is reported as a value between 000 to 500 for the PC scale, and as a value between 001 to 018 for the BG scale.

Fifth Digit—Off-Color Descriptor

The off-color descriptor is assigned as follows: Color match (0), Turbid (1), Greenish Tint (2), Reddish Tint (3), Bluish Tint (4).

CHLORIDE

This number is a measure of the amount of residual inorganic chloride (from soluble lithium chloride by-product) in the product solution, and is measured as parts per million (ppm).

TURBIDITY

This number is a measure of the clarity (or haziness) of the product solution, measured as ntu.

GC ANALYSIS

The product solution is analyzed by quenching a sample into water. This hydrolyzes the lithiated product species in solution to what is called "protonated product". Quenching does not affect the nature of any impurities (i.e., cyclopropane) or unreacted halide in solution. The organic layer of the quench sample is then analyzed by Gas Chromatography (GC). The reported numbers are given as normalized area % for the reported species only, i.e., protonated product, cyclopropane impurity, and unreacted halide. The cyclopropane impurity is only formed in the lithiation reaction of the substrate 2,2-dimethyl-3-(trimethylsiloxy)-1-propyllithium.

EXAMPLE 1

Preparation of 2,2-Dimethyl-3-(trimethylsiloxy)-1-propyllithium in Cyclohexane (Comparative)

A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 5.80 grams, (0.836 mole, 2.8 equivalents), and was transferred to the reaction flask with cyclohexane (272 ml). The reaction mixture was stirred and heated to 65° C. with a heating mantle. The heat source was removed. 1-Chloro-2,2-dimethyl-3-(trimethylsiloxy)-propane (58.08 grams, 0.298 mole, 1.00 equivalent) was added dropwise via the addition funnel. An exotherm was detected after 13.8% of the halide feed had been added. A dry ice/hexane cooling bath was applied as needed to maintain the reaction temperature between 60°–65° C. The total halide feed time was one hundred six minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was a pale yellow color solution, yield=296.94 grams. Total Base=13.5 wt %. Active C—Li=13.0 wt %. Yield=78.0% (based on active analysis). Color=10251. Chloride=524 ppm. Turbidity=117 ntu. GC analysis, quench sample, normalized area% for reported species: protonated product, 91.2%; cyclopropane impurity, 3.6%; unreacted halide, 5.2%.

EXAMPLE 2

Preparation of 2,2-Dimethyl-3-(trimethylsiloxy)-1-propyllithium in Cyclohexane Using Tetrahydrofuran (THF) Catalyst A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 6.40 grams, (0.922 mole, 2.8 equivalents), and was transferred to the reaction flask with cyclohexane (307 ml). The reaction mixture was stirred and heated to 65° C. with a heating mantle. The heat source was removed. 1-Chloro-2,2-dimethyl-3-(trimethylsiloxy)-propane (64.09 grams, 0.329 mole, 1.00 equivalent), containing THF (0.237 grams, 0.0033 mole, 0.01 equivalent), was added dropwise via the addition funnel. An exotherm was detected after 8.3% of the halide feed had been added. A dry ice/hexane cooling bath was applied as needed to maintain the reaction temperature between 60°–65° C. The total halide feed time was eighty-three minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was a clear, pale yellow color solution, yield=317.81 grams. Total Base=15.8 wt %. Active C—Li=15.5 wt %. Yield=90.1% (based on active analysis). Color=10251. Chloride=128 ppm. Turbidity=96 ntu. GC analysis, quench sample, normalized area% for reported species: protonated product, 98.6%; cyclopropane impurity, 0.9%; unreacted halide, 0.5%.

EXAMPLE 3

Preparation of 2,2-Dimethyl -3-(trimethylsiloxy) -1 -propyllithium in Cyclohexane Using Tert-butyl Methyl Ether (MTBE) Catalyst A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 7.00 grams, (1.009 mole, 2.8 equivalents), and was transferred to the reaction flask with cyclohexane (340 ml). The reaction mixture was stirred and heated to 65° C. with a heating mantle. The heat source was removed. 1-Chloro-2,2-dimethyl-3-(trimethylsiloxy)-propane (70.10 grams, 0.360 mole, 1.00 equivalent), containing MTBE (0.952 grams, 0.0108 mole, 0.03 equivalent), was added dropwise via the addition funnel. An exotherm was detected after 11.1% of the halide feed had been added. A dry ice/hexane cooling bath was applied as needed to maintain the reaction temperature between 60°–65° C. The total halide feed time was one hundred eleven minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was a clear, pale yellow color solution, yield=346.57 grams.

Total Base=16.2 wt %. Active C—Li=15.9 wt %. Yield= 92.1% (based on active analysis). Color=10251. Chloride= 51 ppm. Turbidity=75 ntu. GC analysis, quench sample, normalized area% for reported species: protonated product, 97.7%; cyclopropane impurity, 1.2%; unreacted halide, 1.0%.

EXAMPLE 4

Preparation of 2,2-Dimethyl-3-(trimethylsiloxy)-1-propyllithium in Cyclohexane Using Ethylene Glycol Diethyl Ether (EGDE) Catalyst A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 6.90 grams, (0.994 mole, 2.8 equivalents), and was transferred to the reaction flask with cyclohexane (335 ml). The reaction mixture was stirred and heated to 65° C. with a heating mantle. The heat source was removed. 1-Chloro-2,2-dimethyl-3-(trimethylsiloxy)-propane (69.10 grams, 0.355 mole, 1.00 equivalent), containing ethylene glycol diethyl ether (0.420 grams, 0.0036 mole, 0.01 equivalent), was added dropwise via the addition funnel. An exotherm was detected after 4.1% of the halide feed had been added. A dry ice/hexane cooling bath was applied as needed to maintain the reaction temperature between 60°–65° C. The total halide feed time was seventy-five minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was a clear, pale yellow color solution, yield=344.70 grams. Total Base=16.2 wt %. Active C—Li=14.7 wt %. Yield= 85.9% (based on active analysis). Color=10251. Chloride= 405 ppm. Turbidity=40 ntu. GC analysis, quench sample, normalized area % for reported species: protonated product, 99.3%; cyclopropane impurity, 0.5%; unreacted halide, 0.2%.

EXAMPLE 5

Preparation of 2,2-Dimethyl-3-(trimethylsiloxy)-1-propyllithium in Cyclohexane Using Triethylamine (TEA) Catalyst A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 6.50 grams, (0.936 mole, 2.8 equivalents), and was transferred to the reaction flask with cyclohexane (310 ml). The reaction mixture was stirred and heated to 65° C. with a heating mantle. The heat source was removed. 1-Chloro-2,2-dimethyl-3-(trimethylsiloxy)-propane (65.09 grams, 0.334 mole, 1.00 equivalent), containing triethylamine (0.237 grams, 0.0033 mole, 0.01 equivalent), was added dropwise via the addition funnel. An exotherm was detected after 9.5% of the halide feed had been added. A dry ice/hexane cooling bath was applied as needed to maintain the reaction temperature between 60°–65° C. The total halide feed time was eighty-three minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was a clear, pale yellow color solution, yield=321.55 grams. Total Base=16.2 wt %. Active C—Li=16.1 wt %. Yield= 93.3% (based on active analysis). Color=10250. Chloride= 98 ppm. Turbidity=23 ntu. GC analysis, quench sample, normalized area % for reported species: protonated product, 98.6%; cyclopropane impurity, 0.9%; unreacted halide, 0.5%.

EXAMPLE 6

Preparation of 2,2-Dimethyl-3-(trimethylsiloxy)-1-propyllithium in Cyclohexane (Comparative)

A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 6.50 grams, (0.936 mole, 2.4 equivalents), and was transferred to the reaction flask with cyclohexane (370 ml). The reaction mixture was stirred and heated to 65° C. with a heating mantle. The heat source was removed. 1-Chloro-2,2-dimethyl-3-(trimethylsiloxy)-propane (75.94 grams, 0.390 mole, 1.00 equivalent) was added dropwise via the addition funnel. An exotherm was detected after 13.1% of the halide feed had been added. A dry ice/hexane cooling bath was applied as needed to maintain the reaction temperature between 60°–65° C. The total halide feed time was seventy-three minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was an opaque, white color solution, yield=365.99 grams. Total Base=10.4 wt %. Active C—Li=10.1 wt %. Yield=57.1% (based on active analysis). Color=10751. Chloride=2001 ppm. Turbidity= 407 ntu. GC analysis, quench sample, normalized area % for reported species: protonated product, 70.7%; cyclopropane impurity, 7.5%; unreacted halide, 21.7%.

EXAMPLE 7

Preparation of 2,2-Dimethyl-3-(trimethylsiloxy)-1-propyllithium in Cyclohexane Using Hexamethyldisiloxane (HMDS (O)) Catalyst A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 6.10 grams, (0.879 mole, 2.4 equivalents), and was transferred to the reaction flask with cyclohexane (345 ml). The reaction mixture was stirred and heated to 65° C. with a heating mantle. The heat source was removed. 1-Chloro-2,2-dimethyl-3-(trimethylsiloxy)-propane (71.27 grams, 0.366 mole, 1.00 equivalent), containing hexamethyldisiloxane (0.595 grams, 0.0037 mole, 0.01 equivalent), was added dropwise via the addition funnel. An exotherm was detected after 8.9% of the halide feed had been added. A dry ice/hexane cooling bath was applied as needed to maintain the reaction temperature between 60°–65° C. The total halide feed time was ninety-one minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was a hazy solution with very little color, yield= 353.59 grams. Total Base=15.0 wt %. Active C—Li=14.7 wt %. Yield =85.5% (based on active analysis). Color=10251. Chloride=179 ppm. Turbidity=264 ntu. GC analysis, quench sample, normalized area % for reported species: protonated product, 94.9%; cyclopropane impurity, 4.0%; unreacted halide, 1.0%.

EXAMPLE 8

Preparation of 3-(Tert-butyldimethylsiloxy)-1-propyllithium in Cyclohexane (Comparative)

A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 6.00 grams, (0.864 mole, 2.4 equivalents), and was transferred to the reaction flask with cyclohexane (365 ml). The reaction mixture was stirred and heated to 65° C. with a heating mantle. The heat source was removed. 3-(tert-butyldimethylsiloxy)-1-chloro-propane (75.22 grams, 0.360 mole, 1.00 equivalent) was added dropwise via the addition funnel. An exotherm was detected after 8.4% of the halide feed had been added. A dry ice/hexane cooling bath was applied as needed to maintain the reaction temperature between 60°–65° C. The total halide feed time was eighty-nine minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was a pale yellow color solution, yield=362.44 grams. Total Base=13.5 wt %. Active C—Li= 12.4 wt %. Yield=75.2% (based on active analysis). Color= 20031. Chloride=347 ppm. Turbidity=80 ntu. GC analysis, quench sample, normalized area % for reported species: protonated product, 75.1%; unreacted halide, 24.9%.

EXAMPLE 9

Preparation of 3-(Tert-butyldimethylsiloxy)-1-propyllithium in Cyclohexane Using Ethylene Glycol Diethyl Ether (EGDE) Catalyst A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (1×100 ml). The resultant lithium dispersion was dried in a stream of argon, weighed 5.70 grams, (0.821 mole, 2.4 equivalents), and was transferred to the reaction flask with cyclohexane (321 ml). The reaction mixture was stirred and heated to 65° C. with a heating mantle. The heat source was removed. 3-(tert-butyl-dimethylsiloxy)-1-chloro-propane (71.46 grams, 0.342 mole, 1.00 equivalent) containing ethylene glycol diethyl ether (0.404 grams, 0.0034 mole, 0.01 equivalent) was added dropwise via the addition funnel. An exotherm was detected after 7.6% of the halide feed had been added. A dry ice/hexane cooling bath was applied as needed to maintain the reaction temperature between 60°–65° C. The total halide feed time was sixty-three minutes. The cooling bath was removed at the end of the halide feed. The reaction temperature fell off gradually to room temperature. The reaction mixture was stirred for 2 hours. The reaction mixture was transferred with argon pressure to a dry, sintered glass pressure filter. The product solution was pressure filtered with three psi argon. The lithium chloride muds were reslurried with fresh cyclohexane (2×30 ml). The filtrate was a pale yellow color solution, yield=361.94 grams. Total Base=13.7 wt %. Active C—Li=12.4 wt %. Yield=79.0% (based on active analysis). Color=20031. Chloride=307 ppm. Turbidity=70 ntu. GC analysis, quench sample, normalized area % for reported species: protonated product, 79.6%; unreacted halide, 20.4%.

EXAMPLE 10

Preparation of N-(3-lithiopropyl)-2,2,5,5-tetramethyl -2,5-disila-1-azacyclopentane in Cyclohexane (Comparative)

A 500 ml, three-neck Morton flask was fitted with a mechanical stirrer, a 125 ml pressure-equalizing addition funnel, a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion was washed free of mineral oil with hexane (3×100 ml), and pentane (2×100 ml). The resultant lithium dispersion was dried in a stream of argon, weighed 2.55 grams, (0.367 mole, 3.1 equivalents), and was transferred to the reaction flask with cyclohexane (175 ml). The reaction mixture was stirred and heated to reflux 82°–83° C. with a heating mantle. N-(3-chloropropyl)-2,2, 5,5-tetramethyl-2,5-disila-1-azacyclopentane (28.52 grams, 0.119 mole, 1.00 equivalent) was added dropwise via the addition funnel. An exotherm was detected after 34% of the halide feed had been added. The halide feed rate was adjusted as necessary to maintain a reflux reaction temperature (82°–84° C.). The total halide feed time was twenty-seven minutes. The heat source was removed at the end of the halide feed. The reaction temperature fell off gradually to room temperature. The reaction mixture was stirred for 4 hours. The reaction mixture was transferred with argon pressure to a dry, sintered glass pressure filter. The product solution was pressure filtered with three psi argon. The lithium chloride muds were reslurried with fresh cyclohexane (1×30 ml). The liltrate was a pale yellow color solution, yield=157.47 grams. Total Base=15.2 wt %. Active C—Li= 12.0 wt %. Yield=76.7% (based on active analysis). Chloride=168 ppm. GC analysis, quench sample, normalized area % for reported species: protonated product, 91.5%; unreacted halide, 8.5%.

EXAMPLE 11

Preparation of N-(3-lithiopropyl)-2,2,5,5-tetramethyl -2,5-disila-1-azacyclopentane in Cyclohexane Using Tetrahydrofuran (THF) Catalyst A 500 ml, three-neck Morton flask is fitted with a mechanical stirrer, a 125 ml pressure-equalizing addition funnel, a Claisen adapter equipped with a thermocouple, a dry ice condenser, and an argon inlet. This apparatus is dried in an oven overnight at 125° C., assembled hot, and allowed to cool to room temperature in a stream of argon. Lithium metal dispersion is washed free of mineral oil with hexane (3×100 ml), and pentane (2×100 ml). The resultant lithium dispersion is dried in a stream of argon, weighed 2.90 grams (0.418 mole, 2.8 equivalents), and is transferred to the reaction flask with cyclohexane (230 ml). The reaction mixture is stirred and heated to reflux 82°–83° C. with a heating mantle. N-(3-chloropropyl)-2,2,5,5-tetramethyl-2,5-disila-1-azacyclopentane (35.21 grams, 0.149 mole, 1.00 equivalent) containing THF (0.086 grams, 0.0012 mole, 0.01 equivalent) is added dropwise via the addition funnel. The halide feed rate is adjusted as necessary to maintain a reflux reaction temperature (82°–84° C.). The heat source is removed at the end of the halide feed. The reaction temperature is allowed to fall off gradually to room temperature. The reaction mixture is stirred for 4 hours. The reaction mixture is transferred with argon pressure to a dry, sintered glass pressure filter. The product solution is pressure filtered with three psi argon. The lithium chloride muds are reslurried with fresh cyclohexane (1×30 ml). The filtrate is a pale yellow color solution, yield=163.78 grams. Total Base=14.0 wt %. Active C—Li=13.2 wt %. Yield=87.6% (based on active analysis). Chloride=93 ppm. GC analysis, quench sample, normalized area % for reported species: protonated product, 98.3%; unreacted halide, 1.7%.

That which is claimed is:

1. A process for the preparation of functionalized alkyllithium compounds, comprising:

reacting in an inert solvent a protected functionalized alkyl halide with an alkali metal in the presence of a catalytic compound of the formula

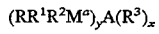

wherein R, $R^1$ and $R^2$ are each independently selected from the group consisting of hydrogen, halogen, alkyl or alkenyl groups containing one to thirteen carbon atoms; $R^3$ is independently selected from aryl groups containing 6 to 18 carbon atoms, four to six-membered heterocyclic carbon containing groups containing one to two heteroatoms selected from oxygen, nitrogen and sulfur; hydroxyalkyl, alkoxyalkyl, monoalkylaminoalkyl, dialkylaminoalkyl and dialkylphosphinoalkyl groups containing two to thirteen carbon atoms; $M^a$ is an element selected from Group IVA of the Periodic Table of Elements; A is selected from oxygen, sulfur, nitrogen, and phosphorus; x+y equal the valence of A; and x and y may independently have a value from zero to three, to produce a functionalized alkylalkali metal compound.

2. The process of claim 1, wherein the catalytic compound is selected from the group consisting of hydrocarbyl ethers, hydrocarbyl silyl ethers, silyl ethers, hydrocarbylamines, hydrocarbyl silyl amines, organosilylamines, hydrocarbyl sulfides, hydrocarbyl thioethers, hydrocarbyl silyl thioethers, silyl thioethers, hydrocarbyl phosphines, and mixtures thereof.

3. The process of claim 1, wherein the compound $(RR^1R^2M^a)_yA(R^3)_x$ is a hydrocarbyl ether.

4. The process of claim 3, wherein the hydrocarbyl ether is selected from the group consisting of tetrahydrofuran, 2-methyl tetrahydrofuran, 1,4-dioxane, tetrahydropyran, diethyl ether, dimethyl ether, methyl-t-butyl ether, di-n-butyl ether, diamyl ether, di-n-hexyl ether, di-n-octyl ether, anisole, butylphenyl ether, diphenyl ether, the di-methyl, ethyl, and butyl ethers of ethylene glycol, diethylene glycol, and triethylene glycol, dimethoxymethane, diethoxymethane, and mixtures thereof.

5. The process of claim 3, wherein the hydrocarbyl ether is tetrahydrofuran.

6. The process of claim 3, wherein the hydrocarbyl ether is tert-butyl methyl ether.

7. The process of claim 3, wherein the hydrocarbyl ether is ethylene glycol diethyl ether.

8. The process of claim 1, wherein the compound $(RR^1R^2M^a)_yA(R^3)_x$ is a hydrocarbylamine.

9. The process of claim 8, wherein the hydrocarbylamine is selected from the group consisting of triethylamine, tributylamine, trihexylamine, trimethylamine, methyldibutylamine, N,N,N'N'-tetramethylethylenediamine, pentamethyldiethylenetriamine, N,N-dimethylaniline, diisopropylethylamine, 1,4-diazabicyclo[2.2.2]octane, N-methylpiperidine, N-ethylpyrrolidine, and mixtures thereof.

10. The process of claim 8, wherein the hydrocarbylamine is triethylamine.

11. The process of claim 1, wherein the compound $(RR^1R^2M^a)_yA(R^3)_x$ is a hydrocarbylsilyl ether or silyl ether.

12. The process of claim 11, wherein the hydrocarbylsilyl or silyl ether is selected from the group consisting of t-butyldimethylisopropoxysilane, trimethylisopropoxysilane, chlorodimethylisopropoxysilane, hexamethyldisiloxane, hexaethyldisiloxane, and mixtures thereof.

13. The process of claim 11, wherein the hydrocarbylsilyl or silyl ether is hexamethyldisiloxane.

14. The process of claim 1, wherein the compound $(RR^1R^2M^a)_yA(R^3)_x$ is a hydrocarbylsilylamine.

15. The process of claim 14, wherein the hydrocarbylsilyl amine is selected from the group consisting of heptamethyldisilazane, N,N-diethyltrimethylsilylamine, N,N-dimethyltriethylsilylamine, N-methyl-2,2,5,5-tetramethyl-2,5,-disila-1-azacylclopentane, and mixtures thereof.

16. The process of claim 1, wherein the compound $(RR^1R^2M^a)_yA(R^3)_x$ is a hydrocarbyl sulfide.

17. The process of claim 16, therein the hydrocarbyl sulfide is selected from the group consisting of diethyl sulfide, dibutyl sulfide, tetrahydrothiophene, 1,4-dithiane, 1,4-thioxane, and mixtures thereof.

18. The process of claim 1, wherein the compound $(RR^1R^2M^a)_y(R^3)_x$ is a hydrocarbylphosphine.

19. The process of claim 18, wherein the hydrocarbyl phoshine is selected from the group consisting of triethylphosphine, tributylphosphine, tricyclohexylphosphine, p-methylcyclopentamethylenephosphine, 1,2-bis(dimethylphosphino)ethane, and mixtures thereof.

20. The process of claim 1, wherein the catalytic compound is present in an amount of about 0.1 to about 10 mole percent.

21. The process of claim 20, wherein the catalytic compound is present in an amount less than or about 1 mole percent.

22. The process of claim 1, wherein the protected functionalized alkyl halide is a compound of the formula

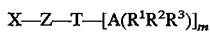

wherein X is halide; Z is a branched or straight chain hydrocarbon group containing 3–25 carbon atoms, optionally containing aryl or substituted aryl groups; T is oxygen, sulfur, or nitrogen; A is an element selected from Group IVa of the Periodic Table of Elements; $R^1$, $R^2$, and $R^3$ are each independently selected from hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, and cycloalkyl and substituted cycloalkyl containing 5 to 12 carbon atoms; and m is dependent on the valence of T and varies from one when T is oxygen or sulfur to two when T is nitrogen.

23. The process of claim 22, further comprising reacting the functionalized alkylalkali metal compound with a compound selected from the group consisting of conjugated diene hydrocarbons, alkenyl substituted aromatic hydrocarbons, and mixtures thereof, to provide a compound of the formula $M—Q_n—Z—T—[A(R^1R^2R^3)]_m$, wherein Q is a saturated or unsaturated hydrocarbyl group derived by incorporation of a compound selected from the group consisting of conjugated diene hydrocarbons, alkenylsubstituted aromatic hydrocarbons, and mixtures thereof; n is an integer from 0 to 5; M is an alkali metal; and Z, T, A, $R^1$, $R^2$, $R^3$ and m are as defined in claim 22.

24. The process of claim 22, wherein the protected functionalized alkyl halide is selected from the group consisting of tertiary amino-1-haloalkanes, omega-hydroxy-protected-1-haloalkanes, omega-thio-protected-1-haloatkanes, omega-hydroxy-silyl-protected-1-haloalkanes, and mixtures thereof.

25. The process of claim 1, wherein the functionalized alkylalkali metal compound is a compound of the formula

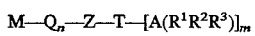

wherein M is an alkali metal; Q is a saturated or unsaturated hydrocarbyl group derived by incorporation of a compound selected from the group consisting of conjugated diene hydrocarbons, alkenylsubstituted aromatic hydrocarbons, and mixtures thereof; n is an integer from 0 to 5; Z is a branched or straight chain hydrocarbon group which contains 3–25 carbon atoms, optionally containing aryl or substituted aryl groups; T is oxygen, sulfur, or nitrogen; A is an element selected from Group IVa of the Periodic Table of Elements; $R^1$, $R^2$, and $R^3$ are each independently selected from hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, and cycloalkyl and substituted cycloalkyl containing 5 to 12 carbon atoms; and m is dependent on the valence of T and varies from one when T is oxygen or sulfur to two when T is nitrogen.

26. The process of claim 1, wherein the alkali metal is lithium.

27. The process of claim 1, wherein said reacting step is conducted at a temperature between about 35° C. and about 130° C.

28. The process of claim 1, wherein said reacting step is conducted at the solvent reflux temperature.

29. The process of claim 1, wherein the inert solvent is a hydrocarbon solvent selected from the group consisting of alkane, cycloalkane, and aromatic solvents having from 5 to 10 carbon atoms, and mixtures thereof.

30. The process of claim 25, wherein A is carbon or silicon.

31. The process of claim 25, wherein the functionalized alkylalkali metal compound is selected from the group consisting of omega-(tert-alkoxy)-1-alkyllithiums, omega-(tert-alkoxy)-1-alkyllithiums chain extended with conjugated alkadienes, alkenylsubstituted aromatic hydrocarbons, and mixtures thereof, omega-(tert-alkylthio)-1-alkyllithiums, omega-(tert-alkylthio)-1-alkyllithiums chain extended with conjugated alkadienes, alkenylsubstituted aromatic hydrocarbons, and mixtures thereof, omega-(tert-butyldimethylsilyloxy)-1-alkyllithiums, omega-(tert-butyldimethylsilylthio)-1-alkyllithiums, omega-(dialkylamino)-1-alkyllithiums, omega-(dialkylamino)-1-alkyllithiums chain-extended with conjugated alkadienes, alkenylsubstituted aromatic hydrocarbons, and mixtures thereof, and omega-(bis-tert-alkylsilylamino)-1-alkyllithiums.

32. The process of claim 25, wherein the functionalized alkylalkali metal compound is selected from the group consisting of 2,2-dimethyl-3-(trimethylsiloxy)-1-propyllithium, 3-(tert-butyldimethylsiloxy)-2,2-dimethyl-propyllithium, 3-(tert-butyldimethylsiloxy)-1-propyllithium, 6-(tert-butyldimethylsiloxy)-1-hexyllithium, 3-(tert-butyloxy)-1-hexyllithium, and N-(3-lithiopropyl)-2,2,5,5-tetramethyl-2,5-disila-1-azacyclopentane.

33. The process of claim 1, wherein the functionalized alkylalkali metal compound is 2,2-dimethyl-3-(trimethylsiloxy)-1-propyllithium.

34. The process of claim 1, wherein the functionalized alkylalkali metal compound is 3-(tert-butyldimethylsiloxy)-1-propyllithium.

35. The process of claim 1, wherein the functionalized alkylalkali metal compound is N-(3-lithiopropyl)-2,2,5,5-tetramethyl-2,5-disila-1-azacyclopentane.

36. A process for the preparation of functionalized alkyllithium compounds, comprising reacting in an inert solvent a protected functionalized alkyl halide of the formula

wherein X is halide; Z is a branched or straight chain hydrocarbon group containing 3–25 carbon atoms, optionally containing aryl or substituted aryl groups; T is oxygen, sulfur, or nitrogen; A is an element selected from Group IVa of the Periodic Table of Elements; $R^1$, $R^2$, and $R^3$ are each independently selected from hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, and cycloalkyl and substituted cycloalkyl containing 5 to 12 carbon atoms; and m is dependent on the valence of T and varies from one when T is oxygen or sulfur to two when T is nitrogen, with lithium in the presence of a catalytic compound selected from the group consisting of tetrahydrofuran, tert-butyl methyl ether, ethylene glycol diethyl ether, triethylamine, and hexamethyldisiloxane to produce a functionalized alkyllithium compound.

37. The process of claim 36, wherein said functionalized alkyllithium compound has the formula M'Z—T—[A(R¹R²R³)]$_m$, wherein M is lithium, and Z, T, A, R¹, R², R³ and m are as defined in claim 36.

38. The process of claim 36, wherein the functionalized alkyllithium compound is 2,2-dimethyl-3-(trimethylsiloxy)-1-propyllithium.

39. The process of claim 36, wherein the functionalized alkyllithium compound is 3-(tert-butyldimethylsiloxy)-1-propyllithium.

40. The process of claim 36, wherein the functionalized alkyllithium compound is N-(3-lithiopropyl)-2,2,5,5-tetramethyl-2,5-disila-1-azacyclopentane.

41. The process of claim 37, further comprising reacting the functionalized alkyllithium compound with a compound selected from the group consisting of conjugated diene hydrocarbons, alkenyl substituted aromatic hydrocarbons, and mixtures thereof, to provide a compound of the formula M—Q$_n$—Z—T—[A(R¹R²R³)]$_m$, wherein Q is a saturated or unsaturated hydrocarbyl group derived by incorporation of a compound selected from the group consisting of conjugated diene hydrocarbons, alkenylsubstituted aromatic hydrocarbons, and mixtures thereof; n is an integer from 0 to 5; and M, Z, T, A, R¹, R², R³ and m are as defined in claim 37.

42. A composition comprising:

a functionalized alkylalkali metal compound of the formula

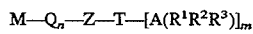

wherein M is an alkali metal; Q is a saturated or unsaturated hydrocarbyl group derived by incorporation of a compound selected from the group consisting of conjugated diene hydrocarbons, alkenylsubstituted aromatic hydrocarbons, and mixtures thereof; n is an integer from 0 to 5; Z is a branched or straight chain hydrocarbon group which contains 3–25 carbon atoms, optionally containing aryl or substituted aryl groups; T is oxygen, sulfur, or nitrogen; A is an element selected from Group IVa of the Periodic Table of Elements; R¹, R², and R³ are each independently selected from hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, and cycloalkyl and substituted cycloalkyl containing 5 to 12 carbon atoms; and m is dependent on the valence of T and varies from one when T is oxygen or sulfur to two when T is nitrogen; and a compound of the formula

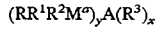

wherein R, R¹ and R² are each independently selected from the group consisting of hydrogen, halogen, alkyl or alkenyl groups containing one to thirteen carbon atoms; R³ is independently selected from aryl groups containing 6 to 18 carbon atoms, four to six-membered heterocyclic carbon containing groups containing one to two heteroatoms selected from oxygen, nitrogen and sulfur; hydroxyalkyl, alkoxyalkyl, monoalkylaminoalkyl, dialkylaminoalkyl, and dialkylphosphinoalkyl groups containing two to thirteen carbon atoms; M$^a$ is an element selected from Group IVA of the Periodic Table of Elements; A is selected from oxygen, sulfur, nitrogen, and phosphorus; x+y equal the valence of A; and x and y may independently have a value from zero to three, in an inert solvent.

43. The composition of claim 42, wherein said compound of the formula (RR¹R²M$^a$)$_y$(R³)$_x$ is present in the composition in an amount of about 0.1 to about 10 mole percent.

44. The composition of claim 42, wherein said compound of the formula (RR¹R²M$^a$)$_y$A(R³)$_x$ is present in the composition in an amount less than or about 1 mole percent.

45. The composition of claim 42, wherein the functionalized alkylalkali metal compound is selected from the group consisting of omega-(tert-alkoxy)-1-alkyllithiums, omega-(tert-alkoxy)-1-alkyllithiums chain extended with conjugated alkadienes, alkenylsubstituted aromatic hydrocarbons, and mixtures thereof, omega-(tert-alkylthio)-1-alkyllithiums, omega-(tert-alkylthio)-1-alkyllithiums chain extended with conjugated alkadienes, alkenylsubstituted aromatic hydrocarbons, and mixtures thereof, omega-(tert-butyldimethylsilyloxy)-1-alkyllithiums, omega-(tert-butyldimethylsilylthio)-1-alkyllithiums, omega-(dialkylamino)-1-alkyllithiums, omega-(dialkylamino)-1-alkyllithiums chain-extended with conjugated alkadienes, alkenylsubstituted aromatic hydrocarbons, and mixtures thereof, and omega-(bis-tert-alkylsilylamino)-1-alkyllithiums.

46. The composition of claim 42, wherein the functionalized alkylalkali metal compound is selected from the group consisting of 2,2-dimethyl-3-(trimethylsiloxy)-1-propyllithium, 3-(tert-butyldimethylsiloxy)-2,2-dimethylpropyllithium, 3-(tert-butyldimethylsiloxy)-1-propyllithium, 6-(tert-butyldimethylsiloxy)-1-hexyllithium, 3-(tert-butyloxy)-1-hexyllithium, and N-(3-lithiopropyl)-2,2,5,5-tetramethyl-2,5-disila-1-azacyclopentane.

47. The composition of claim 42, wherein the functionalized alkylalkali metal compound is 2,2-dimethyl-3-(trimethylsiloxy)-1-propyllithium.

48. The composition of claim 42, wherein the functionalized alkylalkali metal compound is 3-(tert-butyldimethylsiloxy)-1-propyllithium.

49. The composition of claim 42, wherein the functionalized alkylalkali metal compound is N-(3-lithiopropyl)-2,2,5,5-tetramethyl-2,5-disila-1-azacyclopentane.

50. The composition of claim 42, wherein the compound of the formula (RR¹R²M$^a$)$_y$A(R³)$_x$ is selected from the group consisting of hydrocarbyl ethers, hydrocarbyl silyl ethers, silyl ethers, hydrocarbylamines, hydrocarbyl silyl amines, organosilylamines, hydrocarbyl sulfides, hydrocarbyl thioethers, hydrocarbyl silyl thioethers, silyl thioethers, hydrocarbyl phosphines, and mixtures thereof.

51. The composition of claim 42, wherein the compound of formula (RR¹R²M$^a$)$_y$A(R³)$_x$ is a hydrocarbyl ether.

52. The composition of claim 45, wherein the hydrocarbyl ether is selected from the group consisting of tetrahydrofuran, 2-methyl tetrahydrofuran, 1,4-dioxane, tetrahydropyran, diethyl ether, dimethyl ether, methyl-t-butyl ether, di-n-butyl ether, diamyl ether, di-n-hexyl ether, di-n-octyl ether, anisole, butylphenyl ether, diphenyl ether, the di-methyl, ethyl, and butyl ethers of ethylene glycol, diethylene glycol, and triethylene glycol, dimethoxymethane, diethoxymethane, and mixtures thereof.

53. The composition of claim 51, wherein the hydrocarbyl ether is tetrahydrofuran.

54. The composition of claim 51, wherein the hydrocarbyl ether is tert-butyl methyl ether.

55. The composition of claim 42, wherein the compound of formula $(RR^1R^2M^a)_yA(R^3)_x$ is a hydrocarbylamine.

56. The composition of claim 55, wherein the hydrocarbylamine is selected from the group consisting of triethylamine, tributylamine, trihexylamine, trimethylamine, methyldibutylamine, N,N,N'N'-tetramethylethylenediamine, pentamethyldiethylenetriamine, N,N-dimethylaniline, diisopropylethylamine, 1,4-diazabicyclo[2.2.2]octane, N-methylpiperidine, N-ethylpyrrolidine, and mixtures thereof.

57. The composition of claim 55, wherein the hydrocarbylamine is triethyleneamine.

58. The composition of claim 42, wherein the compound of formula $(RR^1R^2M^a)_yA(R^3)_x$ is a hydrocarbylsilyl ether or a silyl ether.

59. The composition of claim 58, wherein the hydrocarbylsilyl ether or silyl ether is selected from the group consisting of t-butyldimethylisopropoxysilane, trimethylisopropoxysilane, chlorodimethylisopropoxysilane, hexamethyldisiloxane, hexaethyldisiloxane, and mixtures thereof.

60. The composition of claim 58, wherein the hydrocarbylsilyl ether or silyl ether is hexamethyldisiloxane.

61. The composition of claim 42, wherein the compound $(RR^1R^2M^a)_yA(R^3)_x$ is a hydrocarbyl silyl amine.

62. The composition of claim 61, wherein the hydrocarbyl silyl amine is selected from the group consisting of heptamethyldisilazane, N,N-diethyltrimethylsilylamine, N,N-dimethyltriethylsilylamine, N-methyl-2,2,5,5-tetramethyl-2,5,-disila-1-azacylclopentane, and mixtures thereof.

63. The composition of claim 42, wherein the compound $(RR^1R^2M^a)_yA(R^3)_x$ is a hydrocarbyl sulfide.

64. The composition of claim 63, wherein the hydrocarbyl sulfide is selected from the group consisting of diethyl sulfide, dibutyl sulfide, tetrahydrothiophene, 1,4-dithiane, 1,4 thioxane, and mixtures thereof.

65. The composition of claim 42, wherein the compound $(RR^1R^2M^a)_yA(R^3)_x$ is a hydrocarbyl phosphine.

66. The composition of claim 65, wherein the hydrocarbyl phosphine is selected from the group consisting of triethylphosphine, tributylphosphine, tricyclohexylphosphine, p-methylcyclopentamethylenephosphine, 1,2-bis(dimethylphosphino)ethane, and mixtures thereof.

67. A composition comprising a functionalized alkylalkali metal compound of the formula $$M-Q_n-Z-T-[A(R^1R^2R^3)]_m$$

wherein M is an alkali metal; Q is a saturated or unsaturated hydrocarbyl group derived by incorporation of a compound selected from the group consisting of conjugated diene hydrocarbons, alkenylsubstituted aromatic hydrocarbons, and mixtures thereof; n is an integer from 0 to 5; Z is a branched or straight chain hydrocarbon group which contains 3–25 carbon atoms, optionally containing aryl or substituted aryl groups; T is oxygen, sulfur, or nitrogen; A is an element selected from Group IVa of the Periodic Table of Elements; $R^1$, $R^2$, and $R^3$ are each independently selected from hydrogen, alkyl, substituted alkyl groups containing lower alkyl, lower alkylthio, and lower dialkylamino groups, aryl or substituted aryl groups containing lower alkyl, lower alkylthio, and lower dialkylamino groups, and cycloalkyl and substituted cycloalkyl containing 5 to 12 carbon atoms; and m is dependent on the valence of T and varies from one when T is oxygen or sulfur to two when T is nitrogen, prepared by reacting in an inert solvent a protected functionalized alkyl halide with an alkali metal in the presence of a catalytic compound of the formula $$(RR^1R^2M^a)_yA(R^3)_x$$

wherein R, $R^1$ and $R^2$ are each independently selected from the group consisting of hydrogen, halogen, alkyl or alkenyl groups containing one to thirteen carbon atoms; $R^3$ is independently selected from aryl groups containing 6 to 18 carbon atoms, four to six-membered heterocyclic carbon containing groups containing one to two heteroatoms selected from oxygen, nitrogen and sulfur; hydroxyalkyl, alkoxyalkyl, monoalkylaminoalkyl, dialkylaminoalkyl and dialkylphosphinoalkyl groups containing two to thirteen carbon atoms; $M^a$ is an element selected from Group IVA of the Periodic Table of Elements; A is selected from oxygen, sulfur, nitrogen, and phosphorus; x+y equal the valence of A; and x and y may independently have a value from zero to three.

* * * * *

UNITED STATES PATENT AND TRADEMARK OFFICE
CERTIFICATE OF CORRECTION

PATENT NO. : 5,663,398

DATED : September 2, 1997

INVENTOR(S) : Schwindeman et al.

It is certified that error appears in the above-identified patent and that said Letters Patent is hereby corrected as shown below:

Column 21, line 49, "haloatkanes" should be -- haloalkanes --.

Column 23, line 12, M'Z-T-[A" should be -- M-Z-T-[A --.

Column 24, line 14, "$(RR^1R^2M^a)_y(R^3)_x$" should be -- $(RR^1R^2M^a)_yA(R^3)_x$ --.

Signed and Sealed this

Twenty-third Day of December, 1997

Attest:

BRUCE LEHMAN

Attesting Officer

Commissioner of Patents and Trademarks